(12) United States Patent
Bhuyan et al.

(10) Patent No.: US 10,266,459 B2
(45) Date of Patent: Apr. 23, 2019

(54) PRODUCTION OF PROPYLENE IN A FLUID CATALYTIC CRACKING UNIT

(71) Applicant: Indian Oil Corporation Limited, Bandra (East), Mumbai (IN)

(72) Inventors: Manoj Kumar Bhuyan, Faridabad (IN); Satheesh Vetterkunnel Kumaran, Faridabad (IN); Debasis Bhattacharyya, Faridabad (IN); Shoeb Hussain Khan, Faridabad (IN); Bidyut De, Faridabad (IN); Sudhir Kumar Pande, Faridabad (IN)

(73) Assignee: Indian Oil Corporation Limited, Bandra (East) (IN)

( * ) Notice: Subject to any disclaimer, the term of this patent is extended or adjusted under 35 U.S.C. 154(b) by 13 days.

(21) Appl. No.: 15/681,832

(22) Filed: Aug. 21, 2017

(65) Prior Publication Data

US 2018/0050969 A1 Feb. 22, 2018

(30) Foreign Application Priority Data

Aug. 19, 2016 (IN) .............................. 201621028347

(51) Int. Cl.
*C07C 4/06* (2006.01)
*C07C 2/08* (2006.01)
(Continued)

(52) U.S. Cl.
CPC ................ *C07C 4/06* (2013.01); *C10G 11/18* (2013.01); *C10G 11/187* (2013.01); *C10G 57/02* (2013.01);
(Continued)

(58) Field of Classification Search
None
See application file for complete search history.

(56) References Cited

U.S. PATENT DOCUMENTS 4,328,384 A * 5/1982 Daviduk .................... B01J 8/26
585/469
4,966,680 A 10/1990 Avidan et al.
(Continued)

FOREIGN PATENT DOCUMENTS

WO WO 2010/067379 6/2010
WO WO 2013/054173 4/2013

*Primary Examiner* — Philip Y Louie
(74) *Attorney, Agent, or Firm* — Workman Nydegger

(57) ABSTRACT

A process and apparatus for catalytic cracking of hydrocarbon feedstock employing circulating fluidized bed reactor-regenerator configuration for maximizing the yield of propylene (C3 olefin) is disclosed. The apparatus comprises two reaction zones operating under different temperature and weight hourly space velocity (WHSV), one primary zone for cracking of hydrocarbon feedstock and other as secondary zone for cracking of C4 fraction produced from the cracking of hydrocarbon feedstock in the primary reaction zone, optionally admixed with C4 stream from external source. Two dedicated conduits equipped with valves for control of catalyst flow rate are provided to supply the hot catalyst from a common catalyst regeneration zone wherein the catalyst flowing though conduit connected to the secondary reaction zone is cooled employing a heat exchanging device. The lower temperature achieved in secondary reaction zone on account of exchange of heat along with lower weight hourly space velocity (WHSV) selectively promotes oligomerization of C4 fraction before being cracked to produce C3 olefin in the subsequent portion of the reaction zone (primary).

8 Claims, 2 Drawing Sheets

(51) Int. Cl.
*C10G 57/02* (2006.01)
*C10G 11/18* (2006.01)

(52) U.S. Cl.
CPC ...... *C07C 2529/08* (2013.01); *C07C 2529/40* (2013.01); *C07C 2529/80* (2013.01); *C10G 2300/4081* (2013.01); *C10G 2400/20* (2013.01)

(56) References Cited

U.S. PATENT DOCUMENTS

| | | | |
|---|---|---|---|
| 4,990,314 A * | 2/1991 | Herbst | B01J 8/12 208/113 |
| 5,348,642 A | 9/1994 | Serrand et al. | |
| 5,597,537 A | 1/1997 | Wegerer et al. | |
| 6,059,958 A * | 5/2000 | Ramos | C10G 11/18 208/113 |
| 7,374,660 B2 | 5/2008 | Steffens et al. | |
| 8,163,247 B2 | 4/2012 | Lomas et al. | |
| 2004/0060846 A1 | 4/2004 | Letzsch | |
| 2011/0240523 A1* | 10/2011 | Mandal | C10G 11/18 208/120.01 |
| 2014/0357912 A1* | 12/2014 | Mandal | C10G 11/182 585/302 |

\* cited by examiner

PRODUCTION OF PROPYLENE IN A FLUID CATALYTIC CRACKING UNIT

FIELD OF THE INVENTION

The present invention relates to a process and apparatus for catalytic cracking of hydrocarbon feedstock. More particularly, this invention covers process for catalytic cracking of hydrocarbon by employing circulating fluidized bed reactor-regenerator configuration for maximizing the yield of propylene ($C_3$ olefin).

BACKGROUND OF THE INVENTION

Fluid Catalytic Cracking (FCC) is the most important conversion process used in petroleum refineries. It is widely used to convert the high-boiling, high-molecular weight hydrocarbon fractions of petroleum crude oils to more valuable gasoline, olefinic gases, and other products. Cracking of petroleum hydrocarbons was originally done by thermal cracking, which has been almost completely replaced by catalytic cracking because of its adaptability towards improved and selective cracking to produce high octane gasoline and valuable lighter olefinic gaseous products. This process also provides flexibility to be tuned to different modes of operational window in order to maximize the product of interest.

The conversion section of FCC unit consists of riser, reactor, stripper, regenerator and their associated hardware internals. The feed is injected into the up-flowing catalyst at the bottom of the riser. Steam is introduced along with the feed for proper atomization. The feed molecules are cracked inside the riser when they are contacted with hot regenerated catalyst producing product vapors and coke. The catalyst activity is reduced due to deposition of coke on the catalyst. The cracked products along with the catalyst move up through the riser and the primary disengagement of the catalyst from the hydrocarbon vapor is achieved through riser termination device. The hydrocarbon vapor after separation from catalyst is fed to a fractionation section for separation into various cuts. The separated spent catalyst is steam stripped in stripper to recover trapped hydrocarbons inside the catalyst pores. The stripped spent catalyst flows to regenerator wherein the coke deposited on the spent catalyst is burnt off in presence of air and/or oxygen containing gases to restore the catalyst activity. The hot regenerated catalyst is subsequently recycled back to the riser bottom to complete the cycle.

The demand for light olefins like ethylene and propylene as building blocks for the production of petrochemicals will continue to grow. Propylene demand growth rate outpaces ethylene due to high demand of poly-propylene and other propylene derivatives. The conventional steam cracking units, which are more energy intensive, cannot meet the incremental demand of propylene as its propylene to ethylene ratio is low. Furthermore, much of the new steam cracking capacity is based on ethane feed, which produces little propylene. Therefore, although steam cracking continues to supply most of the world's propylene, there is an increasing need for production of propylene from other sources.

U.S. Pat. No. 5,348,642 discloses a catalytic cracking process and apparatus wherein a part of hot regenerated catalyst is passed directly from the regenerator to the stripping zone via a conduit to increase the stripping zone temperature resulting in improved recovery of hydrocarbons from the spent catalyst.

The conversion of the feed-stocks processed is optimized as per the product slate requirement by designing the reaction of severity, i.e. reactor outlet temperature (ROT) and catalyst to oil ratio (C/O). In a FCC unit, ROT is the measured variable which is achieved by controlling catalyst circulation rate (CCR) to the riser bottom from the regenerator vessel. At constant feed rate, increase in ROT leads to a higher CCR and thus a higher C/O inside the riser. There are prior art inventions where the C/O has been increased without changing ROT.

U.S. Pat. No. 5,597,537 discloses a FCC apparatus which mixes a part of spent catalyst with regenerated catalyst in a separate chamber to obtain a blended catalyst stream before contacting with feed. Mixing of the spent catalyst (normally at lower temperature) with regenerated catalyst (normally at higher temperature) in the mixing chamber results in a lower equilibrium temperature at the riser bottom leading to increase in catalyst circulation rate (CCR) at a given reactor outlet temperature (ROT). However, this prior art doesn't teach cracking of $C_4$ hydrocarbons to $C_3$ olefins.

U.S. Pat. No. 8,163,247 discloses process for contacting feed with mixed catalyst in a secondary reactor that is incorporated into an FCC reactor. The mixed catalyst used in the secondary reactor is regenerated catalyst from a regenerator that regenerates spent catalyst from an FCC reactor that is mixed with spent catalyst from either the FCC reactor or the secondary reactor. The mixing of spent and regenerated catalyst reduces the catalyst temperature and tempers catalyst activity to inhibit both thermal and catalytic cracking reactions.

US20040060846A1 discloses a deep catalytic cracking process to produce increased yields of $C_3$ and $C_4$ olefins at the expense of $C_2$ olefins. In this invention, the riser reactor is configured to have two different radii in order to produce improved selectivity to $C_3$ and $C_4$ olefins as products. In the second broader riser section, Weight hourly space velocity (WHSV) is significantly lowered, so that gasoline range molecules produced in the first narrower section is cracked to produce high yields of the light olefins. However, the prior art does not teach any method that is directed specifically to conversion of $C_4$ hydrocarbons to $C_3$ olefins.

U.S. Pat. No. 7,374,660B2 discloses a process for selectively producing $C_3$ olefins from a cracked naphtha stream. A stream rich in $C_4$ olefins is recycled to a dilute phase reaction zone in the stripping zone separate from the dense phase of the stripping zone to improve the propylene selectivity. However, this prior art doesn't provide any means for achieving optimum temperature and catalyst activity which facilitates maximum propylene yield.

WO2013/054173 covers the process for the production of propylene from cracking of $C_4$ fraction in FCC. For production of propylene from cracking of $C_4$ fraction in FCC, weight hourly space velocity (WHSV), temperature and catalyst activity play the major role. These parameters vary depending on the position where and how the $C_4$ fraction are cracked within FCC. In this invention, an optimum condition of weight hourly space velocity (WHSV), temperature as well as catalyst activity is achieved for enhanced production of propylene from cracking of C4 fraction. This is achieved by cracking $C_4$ hydrocarbons in a reaction zone of optimum weight hourly space velocity (WHSV) (stripper bed) where optimum weight hourly space velocity (WHSV) is achievable. Optimum temperature (higher) and Optimum catalyst activity is achieved in this zone by injecting a part of regenerated catalyst directly into the reaction zone using an additional catalyst transfer line.

WO 2010/067379A2 discloses a process for manufacturing propylene and ethylene in increased yield by cracking an olefinic naphtha stream and main hydrocarbon stock in combination with an olefinic $C_4$ hydrocarbon stream in different zones of one or more risers of an FCC unit. The olefinic $C_4$ hydrocarbon stream is cracked in the acceleration zone of the riser at 600 to 800° C. and by injecting it at the riser bottom in place of lift stream.

U.S. Pat. No. 4,966,680A discloses an integrated catalytic cracking process for upgrading light olefinic crackate gas from a fluidized catalytic cracking unit by integrating with a separate oligomerization reactor. The olefin containing gases from the FCC is processed in the oligomerization reactor to convert the said olefins to gasoline range hydrocarbons and the alkane rich byproduct gases are used as life media in the FCC riser bottom.

In the above prior arts of "Propylene production through $C_4$ cracking", it is tried to achieve a higher temperature for efficient cracking of these $C_4$ molecules. But it is seen that beyond certain temperature, the propylene production doesn't improve. The temperature where the C4 fraction is injected is even higher than that used for cracking of the main hydrocarbon feedstock.

As evident from different literatures, in the reaction steps during conversion of C4 fraction to C3 olefin, oligomerization of C4 olefins is the primary step followed by catalytic cracking to produce C3 olefin. Since the oligomerization step is exothermic, lower temperature will facilitate the desired oligomerization reaction. However, prior art processes utilize the same reaction zone, which is operated at elevated temperature.

The present invention relates to a new process and apparatus for catalytic cracking of hydrocarbon feedstock to produce higher yields of propylene, where-in conversion of recycled/external C4 hydrocarbon fraction has been improved thus producing an overall augmented yield of C3 olefin.

OBJECTIVE OF THE INVENTION

It is the primary objective of the invention to provide a modified process and apparatus to further maximize the propylene yield.

It is the further objective of the invention to facilitate the oligomerisation reaction of recycled/external C4 hydrocarbon fraction with higher selectivity by introducing, a separate in-situ reaction zone, namely the secondary zone operating at lower temperature and weight hourly space velocity (WHSV) at the preceding section of primary reaction zone.

It is the further objective of the invention to provide a process for the enhanced production of $C_3$ olefin by reducing the requirement of lift steam in riser so that it can be retrofitted in any new or existing unit.

SUMMARY OF THE INVENTION

The present invention provides a process to substantially increase the propylene yield through selective conversion of recycled/external C4 hydrocarbon fraction in a FCC unit. Improvement in production of propylene in Fluid Catalytic Cracking units adds value to the overall profitability. In this regard, one of the schemes is to recycle $C_4$ hydrocarbon streams to the cracking zone in order to produce additional propylene.

In the present invention, it has been tried to improve the conversion of C4 hydrocarbon fraction (both recycle & fresh) in order to produce higher amount of C3 olefin. In the reaction steps during conversion of C4 fraction to C3 olefin, oligomerization of C4 olefins is the primary step followed by catalytic cracking of the oligomers to produce C3 olefin. Since the oligomerization step is exothermic, lower temperature will facilitate the desired reaction. In order to facilitate the oligomerisation reaction with higher selectivity, a separate in-situ reaction zone, namely the secondary reaction zone (separate from the primary reaction zone meant for cracking of main hydrocarbon feedstock) operating at lower temperature and weight hourly space velocity (WHSV), is provided at the preceding section of primary reaction zone. The required quantity of catalyst is provided to the secondary reaction zone through an additional dedicated conduit connected with the common regenerator. The lower temperature in the secondary reaction zone is achieved by cooling the catalyst drawn from the regeneration zone. Lower temperature at the secondary reaction zone along with lower weight hourly space velocity (WHSV) promotes oligomerisation of C4 fraction before the cracking of the oligomers to produce C3 olefin in the subsequent portion of the reaction zone (primary reaction zone).

In an aspect of the present invention, the one embodiment of the present invention relates to a process for enhancing the yield of C3 olefin in fluid catalytic cracking of hydrocarbon feedstock, the process comprising the steps: (a) contacting a hydrocarbon feedstock in a primary reaction zone of a riser in the presence of a fluidizable solid microspherical cracking catalyst to produce cracked hydrocarbon products and spent catalyst; (b) separating the spent catalyst from the cracked hydrocarbon products and stripping it with steam to remove the hydrocarbons entrapped inside the spent catalyst pores; (c) separating a C4 hydrocarbon fraction of the cracked hydrocarbon products to obtain a recycle C4 hydrocarbon fraction; (d) burning off the coke deposited on the spent catalyst in a catalyst regenerator to obtain a hot regenerated catalyst; (e) recycling a part of the hot regenerated catalyst into the primary reaction zone and remaining part is cooled to obtain a cooled regenerated catalyst, which is recycled to a secondary reaction zone located at upstream of the primary reaction zone of the riser; (f) contacting the recycle C4 hydrocarbon fraction with the cooled regenerated catalyst in the secondary reaction zone of the riser for oligomerization reaction of the olefinic molecules of the recycle C4 hydrocarbon fraction to obtain oligomers; and (g) lifting the oligomers into the primary reaction zone of the riser in order to get cracked to produce C3 olefin.

Another embodiment of the present invention provides a process for enhancing the yield of C3 olefin in fluid catalytic cracking of hydrocarbon feedstock wherein the flow of the hot regenerated catalyst into the primary reaction zone is controlled to achieve the temperature at the exit of riser in the range of 500 to 650° C.

Another embodiment of the present invention provides a process for enhancing the yield of C3 olefin in fluid catalytic cracking of hydrocarbon feedstock wherein the solid microspherical cracking catalyst comprises not less than 5 wt % pentasil zeolite based additive.

Another embodiment of the present invention provides a process for enhancing the yield of C3 olefin in fluid catalytic cracking of hydrocarbon feedstock wherein the hot regenerated catalyst to the secondary reaction zone is cooled in a catalyst cooler and flow is controlled to achieve the temperature in the range of 350° C. to 450° C. inside the secondary reaction zone.

Another embodiment of the present invention provides a process for enhancing the yield of C3 olefin in fluid catalytic cracking of hydrocarbon feedstock wherein weight hourly space velocity in the secondary reaction zone is maintained below 10 hr$^{-1}$ to promote oligomerisation of the olefinic molecules of the recycle C4 hydrocarbon fraction and the oligomers get cracked in the subsequent primary reaction zone to improve the yield of C3 olefin in the overall unit.

Another embodiment of the present invention provides a process for enhancing the yield of C3 olefin in fluid catalytic cracking of hydrocarbon feedstock wherein the fresh C4 hydrocarbon fraction from external sources is optionally processed in the secondary reaction zone along with the recycle C4 hydrocarbons fraction.

Another embodiment of the present invention provides a process for enhancing the yield of C3 olefin in fluid catalytic cracking of hydrocarbon feedstock wherein the fresh C4 hydrocarbon fraction and the recycle C4 hydrocarbon fraction injected into the secondary reaction zone acts as lifting media thus minimizing the requirement of lift steam.

Another embodiment of the present invention provides a process for enhancing the yield of C3 olefin in fluid catalytic cracking of hydrocarbon feedstock wherein a part of the spent catalyst from a reactor vessel is directed to the catalyst cooler to maintain carbon content of the catalyst in the range of 0.3% to 1% in the secondary reaction zone.

In another aspect of the present invention, the one embodiment of the present invention relates to an apparatus for enhancing the yield of C3 olefin in fluidized catalytic cracking of hydrocarbons, said apparatus comprising: (a) a riser having a primary reaction zone for cracking of hydrocarbon feedstock, and a secondary reaction zone for oligomerization of recycled C4 hydrocarbon fraction and fresh C4 hydrocarbon fraction; (b) a reactor vessel connected to the riser reactor for separating cracked hydrocarbon products from a spent catalyst and stripping of the spent catalyst; (c) a catalyst regenerator for regenerating the spent catalyst; and (d) a catalyst cooler for cooling a part of hot regenerated catalyst.

Another embodiment of the present invention provides an apparatus for enhancing the yield of C3 olefin in fluidized catalytic cracking of hydrocarbons wherein the riser has multiple injection points for injecting fresh C4 hydrocarbon stream and recycle C4 hydrocarbon stream, dilution stream, recycle heavy feed, fresh naphtha stream and recycle naphtha stream.

Another embodiment of the present invention provides an apparatus for enhancing the yield of C3 olefin in fluidized catalytic cracking of hydrocarbons wherein the catalyst cooler is connected to the secondary reaction zone of the riser by means of a conduit having a plug valve to control the flow of cooled regenerated catalyst.

DETAILED DESCRIPTION OF THE INVENTION

The present invention provides a process and an apparatus to substantially increase the C3 olefin (propylene) yield through selective conversion of recycled or external C4 hydrocarbon fraction in a FCC unit.

The invention will now be described in an exemplary and non-limiting embodiment as depicted in the accompanying drawings. There can, however, be other embodiments of the same invention, all of which are deemed covered by this description.

Figure 1:
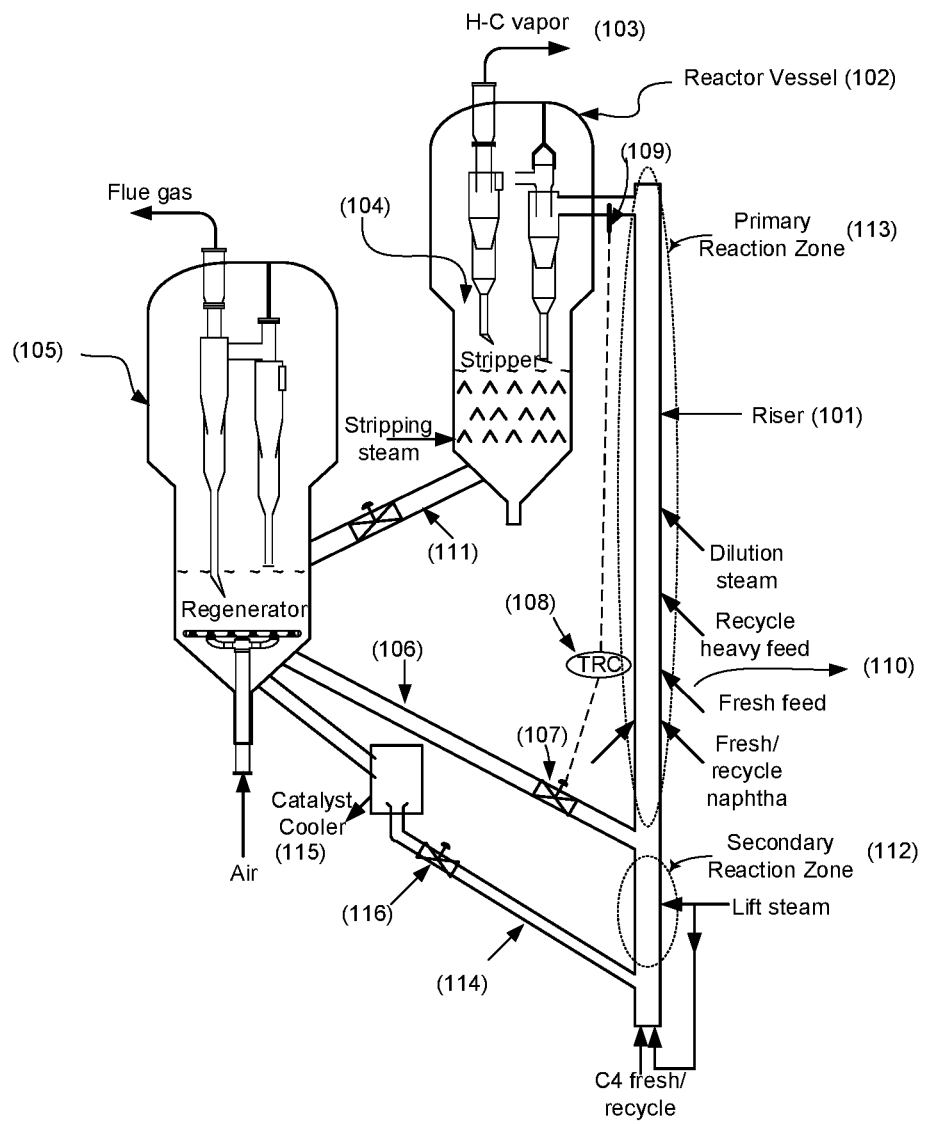
FIGS. 1 & 2 illustrate the Schematic diagram of Riser-Stripper-regenerator section of FCC unit including the additional hardware of a secondary reaction zone and a dedicated cooled regenerated catalyst stand pipe along with a catalyst cooler.

The riser-stripper-regenerator section of the FCC unit is shown in FIG. 1. As in case of normal FCC units, regenerated catalyst is withdrawn from the regenerator (105) via a stand pipe (regenerated catalyst stand pipe) (106) and flows to riser (101) bottom via a control valve (107), which is controlled through a TRC (temperature recorder and controller) (108) in cascade with the temperature measuring element (109) placed at the top of the riser (101). Fresh feed is injected into the up-flowing catalyst in the riser (101) via suitable injectors (110). Vaporization and cracking of the feed takes place as it comes in contact with the hot regenerated catalyst and the whole mixture moves along the riser in upward direction. The hydrocarbon feed is cracked in the riser in presence of fluidizable solid micro-spherical cracking catalyst to produce hydrocarbon products and coke. The riser terminates inside the reactor vessel (102), where in the spent catalyst (catalyst laden with coke generated after reaction) is separated from the product vapors (103) and suitably steam stripped inside stripper (104) before being sent to the regenerator vessel (105) via another standpipe (111). The catalyst is regenerated inside the regeneration vessel by burning off of the coke deposited on the catalyst at a temperature in the range of 680 to 750° C. in presence of air.

As an embodiment of the invention, the riser is elongated further towards the bottom portion to create an additional reaction zone called as 'secondary reaction zone' (112) which is separate from the primary reaction zone (113) meant for cracking of the main hydrocarbon feed. The required quantity of catalyst flow to the secondary reaction zone is provided through an additional dedicated standpipe (114) connected with the common regenerator. This additional standpipe is equipped with a device (115) for cooling of the withdrawn catalyst followed by a control valve (116). Temperature of the cooled regenerated catalyst is targeted to be kept at around 350 to 450° C. which is the targeted temperature of the secondary reaction zone. A C4 hydrocarbon fraction is separated from the cracked hydrocarbon products (103) in the downstream section (not shown) to obtain a recycle C4 hydrocarbon fraction. The recycled/fresh C4 hydrocarbon fraction stream is injected into the secondary reaction zone. Weight hourly space velocity (WHSV) inside the secondary reaction zone (112) is maintained suitably below 10 hr$^{-1}$, preferably between 5 to 10 hr$^{-1}$, Lower temperature and weight hourly space velocity (WHSV) provided at this secondary reaction zone (preceding section of primary reaction zone) helps in promoting the oligomerisation reaction of the C4 olefinic streams with minimal cracking of the oligomers inside this reaction zone. The oligomers formed inside the secondary reaction zone immediately comes into contact with catalyst at higher temperature inside the primary reaction zone (upstream of the cracking of main hydrocarbon feed) to produce desired C3 olefins.

Figure 2:
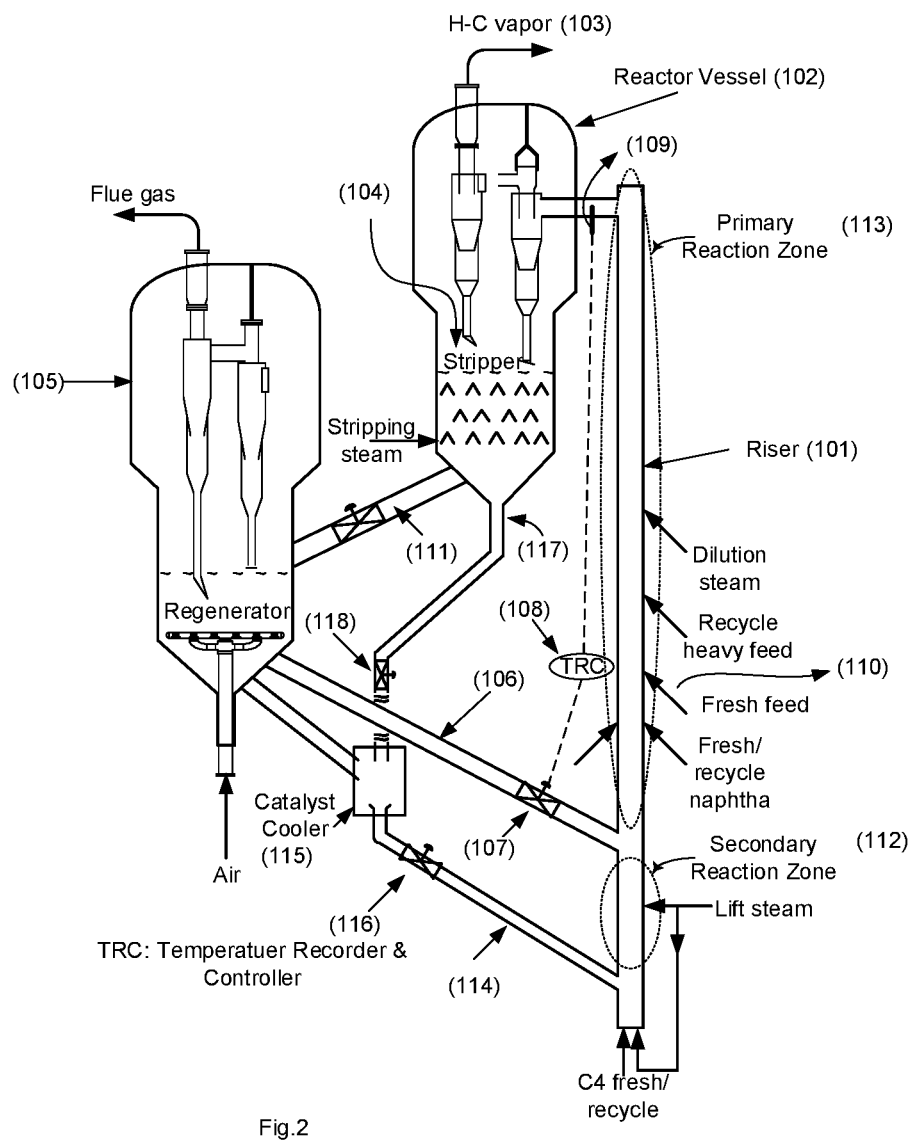

In another embodiment of the invention, as shown in FIG. 2, an additional conduit (117) along with a control valve (118) is envisaged to mix some spent catalyst directly into the catalyst cooler device in order to maintain the carbon content of the catalyst in the range of 0.3 to 1 wt % inside the secondary reaction zone (112). This subside the undesired reactions thus to improve the overall propylene yield from the unit.

In another embodiment of the invention, requirement of lift steam in the riser is reduced by injecting the C4 streams at the same position, where lift steam is injected. Purpose of lift steam is to give an upward thrust to the moving catalyst because of the expansion of steam after injection. Negative aspect of this steam is that it leads to thermal deactivation of the catalyst. By using C4 hydrocarbon stream as lift stream, the thrust effect takes place without any catalyst deactivation effect.

In an embodiment of the invention, the invention provides a process for enhancing the yield of C3 olefin in fluid catalytic cracking of hydrocarbon feedstock, the process comprising:
a) contacting a hydrocarbon feedstock in a primary reaction zone of a riser in the presence of a fluidizable solid micro-spherical cracking catalyst to produce cracked hydrocarbon products and spent catalyst;
b) separating the spent catalyst from the cracked hydrocarbon products and stripping it with steam to remove the hydrocarbons entrapped inside the spent catalyst pores;
c) separating a C4 hydrocarbon fraction of the cracked hydrocarbon products to obtain a recycle C4 hydrocarbon fraction;
d) burning off the coke deposited on the spent catalyst in a catalyst regenerator to obtain a hot regenerated catalyst;
e) recycling a part of the hot regenerated catalyst into the primary reaction zone and remaining part is cooled to obtain a cooled regenerated catalyst, which is recycled to a secondary reaction zone located at upstream of the primary reaction zone of the riser;
f) contacting the recycle C4 hydrocarbon fraction with the cooled regenerated catalyst in the secondary reaction zone of the riser for oligomerization reaction of the olefinic molecules of the recycle C4 hydrocarbon fraction to obtain oligomers; and
g) lifting the oligomers into the primary reaction zone of the riser in order to get cracked to produce C3 olefin.

In an another embodiment of the present invention the flow of the hot regenerated catalyst into the primary reaction zone is controlled to achieve the temperature at the exit of riser in the range of 500 to 650° C.

In an another embodiment of the present invention the solid micro-spherical cracking catalyst comprises not less than 5 wt % pentasil zeolite based additive. Pentasil zeolite based additive present in the solid micro-spherical cracking catalyst preferably in the range of 5 to 50 wt %, more preferably in the range of 10 to 40 wt %.

In an another embodiment of the present invention the hot regenerated catalyst to the secondary reaction zone is cooled in a catalyst cooler and flow is controlled to achieve the temperature in the range of 350° C. to 450° C. inside the secondary reaction zone.

In an another embodiment of the present invention weight hourly space velocity in the secondary reaction zone is maintained below 10 hr$^{-1}$ to promote oligomerisation of the olefinic molecules of the recycle C4 hydrocarbon fraction and the oligomers get cracked in the subsequent primary reaction zone to improve the yield of C3 olefin in the overall unit. Weight hourly space velocity in the secondary reaction zone is preferably maintained between 5 to 10 hr$^{-1}$.

In an another embodiment of the present invention the fresh C4 hydrocarbon fraction from external sources is optionally processed in the secondary reaction zone along with the recycle C4 hydrocarbons fraction.

In an another embodiment of the present invention the fresh C4 hydrocarbon fraction and the recycle C4 hydrocarbon fraction injected into the secondary reaction zone acts as lifting media thus minimizing the requirement of lift steam.

In an another embodiment of the present invention a part of the spent catalyst from a reactor vessel is directed to the catalyst cooler to maintain carbon content of the catalyst in the range of 0.3% to 1% in the secondary reaction zone.

Another aspect of the present invention also discloses an apparatus for enhancing the yield of C3 olefin in fluidized catalytic cracking of hydrocarbons, said apparatus comprising:
a) a riser (101) having a primary reaction zone (113) for cracking of hydrocarbon feedstock, and a secondary reaction zone (112) for oligomerization of C4 hydrocarbon fraction;
b) a reactor vessel (102) connected to the riser reactor (101) for separating cracked hydrocarbon products from a spent catalyst and stripping of the spent catalyst;
c) a catalyst regenerator (105) for regenerating the spent catalyst; and
d) a catalyst cooler (115) for cooling a part of hot regenerated catalyst.

In an another embodiment of the present invention the riser has multiple injection points for injecting fresh C4 hydrocarbon stream and recycle C4 hydrocarbon stream, dilution stream, recycle heavy feed, fresh naphtha stream and recycle naphtha stream.

In an another embodiment of the present invention the catalyst cooler (115) is connected to the secondary reaction zone (112) of the riser (101) by means of a conduit (114) having a plug valve (116) to control the flow of cooled regenerated catalyst.

EXAMPLE

This example demonstrates the improvement in propylene yield in FCCU obtained through cracking of the product $C_4$ stream generated out of cracking of residue feed in the riser using a residue feed having 4.4 wt % conradson carbon residue (CCR) and 941 kg/m$^3$ density. The example given in this section is for illustration purpose only and don't construe to the claims as mentioned in subsequent section.

The data shown in this example have been generated through preliminary engineering calculations based on experimental data from micro—reactor and pilot plant. Base case data is at a reaction temperature of 580° C. and without any $C_4$ cracking. The catalyst used is a mixture of FCC catalyst having average particle size of 80 microns based on USY zeolite and an additive based on pentasil zeolite having silica to alumina molar ratio of 30. The catalyst was hydrothermally deactivated at 810° C. for 5 hrs. The composition of $C_4$ stream used in the study is given in Table-I.

TABLE I

Composition of $C_4$ recycle stream

| Components | wt % |
|---|---|
| i-butane | 23.6 |
| n-butane | 6.5 |
| 1-butene | 15 |
| i-butylene | 26.4 |
| cis-2-butene | 11.7 |
| trans-2-butene | 16 |
| 1,3-butadiene | 0.8 |

The improvements in propylene yield on fresh feed basis with recycle of $C_4$ products using different schemes are presented in Table-II. Case I considers the recycle of $C_4$ stream to the stripper operating at a temperature close to riser outlet temperature. In Case-II, stripper temperature is maintained at a higher temperature than Case-I. Case-III considers $C_4$ recycle to the bottom of the riser so that the $C_4$ cracking reaction is carried out at the upstream of main feed cracking. Case-IV considers the case of the invention, where in the $C_4$ cracking reaction is carried out at two steps. The $C_4$ injection zone temperature is maintained at 350° C.

TABLE II

|  |  | Base case | Case-I | Case-II | Case-III | Case-IV (Invention) |
|---|---|---|---|---|---|---|
| $C_4$ recycle rate | wt % FF | — | 13 | 13 | 13 | 13 |
| Riser Top temperature | ° C. | 580 | 580 | 580 | 580 | 580 |
| $C_4$ injection zone |  | — | Stripper | Stripper | Upstream of main feed injection | Secondary reaction zone (as per invention) at upstream of primary reaction zone (riser) |
| $C_4$ injection zone temperature |  | — | 575 | 600 | 610 | 350 |
| $C_4$ injection zone WHSV | hr$^{-1}$ | — | 10 | 10 | 10 | 10 |
| Propylene Yield | wt % FF | 17.1 | 18.7 | 19.9 | 18.33 | 21.0 |

Using the process of the present invention as depicted in Case-IV, it is found that the propylene production is found to be enhanced w.r.t. the base as well as the other prior art cases. In this example, a residue feed has been used with which ex-riser $C_4$ quantity is coming to be 13 wt %. In the cases of using better quality feed, ex-riser $C_4$ quantity will increase which in turn will make further increase in propylene yield using the present invention.

The invention claimed is:

1. A process for enhancing the yield of C3 olefin in fluid catalytic cracking of hydrocarbon feedstock-, the process comprising:
    a) contacting a hydrocarbon feedstock with a fluidizable solid micro-spherical cracking catalyst in a primary reaction zone of a riser to produce cracked hydrocarbon products and spent catalyst;
    b) separating the spent catalyst from the cracked hydrocarbon products and stripping the spent catalyst with steam in a reactor vessel to remove the cracked hydrocarbons entrapped inside the pores of the spent catalyst;
    c) separating a C4 hydrocarbon fraction from the cracked hydrocarbon products to obtain a recycle C4 hydrocarbon fraction comprising olefinic molecules;
    d) burning off the coke deposited on the spent catalyst in a catalyst regenerator to obtain a hot regenerated catalyst;
    e) recycling a part of the hot regenerated catalyst into the primary reaction zone and cooling a remaining part of the hot regenerated catalyst in a catalyst cooler to obtain a cooled regenerated catalyst, and recycling the cooled regenerated catalyst to a secondary reaction zone of the riser located upstream of the primary reaction zone of the riser;
    f) contacting the recycle C4 hydrocarbon fraction with the cooled regenerated catalyst in the secondary reaction zone of the riser operated at a temperature and weight hourly space velocity lower than that of the primary reaction zone for oligomerization reaction of the olefinic molecules of the recycle C4 hydrocarbon fraction to obtain oligomers; and
    g) lifting the oligomers into the primary reaction zone of the riser for cracking to produce C3 olefin.

2. The process as claimed in claim 1, wherein flow of the hot regenerated catalyst into the primary reaction zone is controlled to achieve a temperature at the exit of the riser in the range of 500° C. to 650° C.

3. The process as claimed in claim 1, wherein the solid micro-spherical cracking catalyst comprises not less than 5 wt % pentasil zeolite based additive.

4. The process as claimed in claim 1, wherein the flow of the cooled regenerated catalyst is controlled to achieve a temperature in the range of 350° C. to 450° C. inside the secondary reaction zone.

5. The process as claimed in claim 1, wherein weight hourly space velocity in the secondary reaction zone is maintained below 10 hr$^{-1}$ to promote oligomerization of the olefinic molecules of the recycle C4 hydrocarbon fraction and the oligomers get cracked in the subsequent primary reaction zone to improve the yield of C3 olefin.

6. The process as claimed in claim 1, wherein a fresh C4 hydrocarbon fraction from external sources is optionally processed in the secondary reaction zone along with the recycle C4 hydrocarbons fraction.

7. The process as claimed in claim 1, wherein the fresh C4 hydrocarbon fraction and the recycle C4 hydrocarbon fraction are injected into the secondary reaction zone and acts as lifting media thus minimizing the requirement of lift steam.

8. The process as claimed in claim 1, wherein a part of the spent catalyst from the reactor vessel is directed to the catalyst cooler to maintain carbon content of the catalyst in the range of 0.3 wt % to 1 wt % in the secondary reaction zone.

* * * * *